United States Patent [19]

Millar et al.

[11] Patent Number: 4,919,672
[45] Date of Patent: Apr. 24, 1990

[54] HIP JOINT AUGMENTATION

[76] Inventors: Edward A. Millar, Box 30, St. Mary's Rd., Libertyville, Ill. 60048; Gerald F. Harris, 3107 S. 122nd St., #7, West Allis, Wis. 53227; Roy G. Fink, 1320 Badgley Rd., Jackson, Mich. 49203

[21] Appl. No.: 300,041
[22] Filed: Jan. 23, 1989
[51] Int. Cl.⁵ ............................ A61F 2/34; A61F 2/30
[52] U.S. Cl. ........................................ 623/22; 623/16; 623/66
[58] Field of Search ..................... 623/16, 18, 20, 22, 623/23

[56] References Cited
U.S. PATENT DOCUMENTS
4,502,161  3/1985  Wall ....................................... 623/22
4,636,215  1/1987  Schwartz ............................... 623/16

FOREIGN PATENT DOCUMENTS
2595241  9/1987  France ................................... 623/22

Primary Examiner—David J. Isabella
Attorney, Agent, or Firm—Beaman & Beaman

[57] ABSTRACT

The invention pertains to a method and apparatus for enhancing the depth of the acetabulum to improve the containment of the femoral head, and the concepts of the invention are employed to correct an unstable hip joint, particularly as occurs with children. A synthetic extracapsular curvalinear prosthesis is affixed to the ilium by fasteners and the prosthesis includes a concave surface corresponding to the configuration of the acetabular socket wherein the prosthesis increases the depth of the acetabulum without disturbing the existing anatomy.

5 Claims, 1 Drawing Sheet

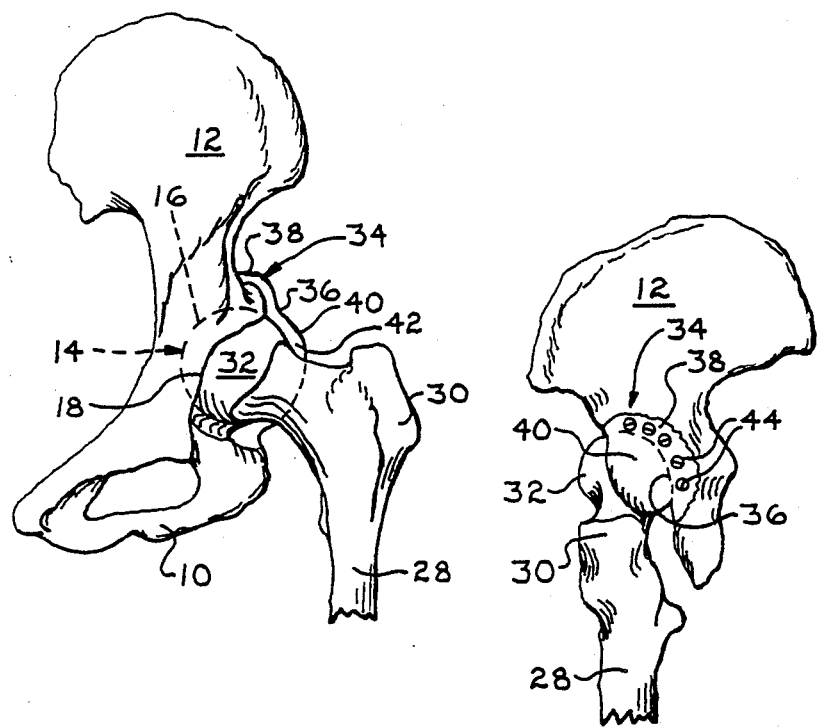
Fig 1
Fig 2
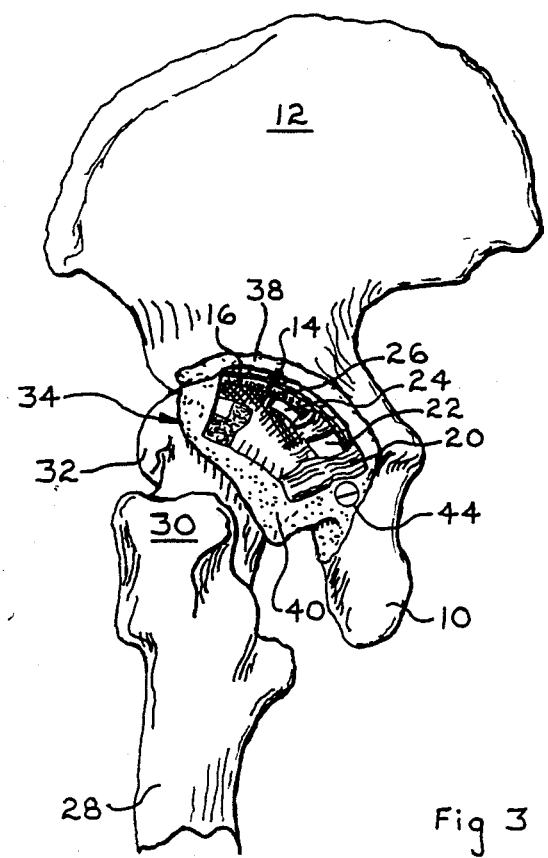
Fig 3

HIP JOINT AUGMENTATION

BACKGROUND OF THE INVENTION

A common crippling ailment of children is an unstable hip joint, i.e. the femoral head or ball of the hip joint does not maintain a normal congruent relationship with the acetabulum or socket defined in the ilium receiving the femoral head. Such instability may occur due to a shallowness of the socket, an abnormal shape of the femoral head; an abnormal geometrical relationship between the femoral head and neck shaft of the femur; a loosening of the retaining joint capsule and ligaments of the joint; an imbalance in the normal muscle or joint forces, or a combination of these factors.

In the past, a number of medical procedures have been developed to overcome an unstable hip joint condition. For instance, the muscle forces may be redirected, the geometry of the femur may be altered to change the direction of force application through the femoral head or the socket may be deepened by extending the rim by the use of bone as commonly referred to as a shelf procedure. Each of these procedures has limitations which are overcome by the practice of the invention.

The desired prosthesis is designed as an augmentative device to be primarily used in children, and is distinct from replacement devices such as those used for acetabular, femoral head or total hip joint replacement.

The object of the invention is to provide an extracapsular curvalinear prosthesis constructed of a high density synthetic material which artificially enhances the depth of the acetabulum and thereby the ability to retain the femoral head, rendering an unstable hip joint stable. The prosthesis is particularly suitable for use with children minimizing the extend of surgery required.

In the practice of the invention a prosthesis formed of a high density polyethylene is attached by staples, screws or other conventional fasteners to the ilium adjacent to the acetabulum. The prosthesis includes an inner concave socket surface corresponding to the femoral head receiving surface of the acetabulum wherein the attachment of the prosthesis to the ilium enhances the depth of the acetabulum as the prosthesis extends beyond the acetabular rim.

The prosthesis is of sufficient configuration as to extend beyond the acetabular rim laterally, posteriorly and superiorly, and adds a sufficient additional shelf for engagement with the femoral head to render a previously unstable hip joint stable.

The prosthesis is of a configuration to be extracapsular and serves as an adjunct to the existing acetabular socket, but does not replace the socket as with a conventional total hip prosthesis. The configuration of the prosthesis obviates the necessity for accurate geometrical fit as is required with a total joint prosthesis in that the natural acetabulum will continue to define the geometry with respect to the femoral head. The prosthesis can be applied to young children wherein the acetabulum is still growing without adversely affecting the growth process.

BRIEF DESCRIPTION OF THE DRAWINGS

The aforementioned objects and advantages of the invention will be appreciated from the following description and accompanying drawings wherein:

FIG. 1 is an anterior view of the ilium, hip bone, femoral head and prosthesis as installed, FIG. 2 is a posterior view of FIG. 1, and FIG. 3 is an enlarged posterior view similar to FIG. 2 with a breakaway view taken through the prosthesis.

DESCRIPTION OF THE PREFERRED EMBODIMENT.

With reference to FIGS. 1-3, the bone structure directly associated with a single hip is illustrated, and the pelvis is indicated at 10 while the ilium is represented at 12. The hip socket or acetabulum 14 is defined in the ilium and includes the concave socket surface 16 and the acetabular rim 18.

The acetabulum 14 is of a generally spherical segment configuration and includes, adjacent to the concave acetabular surface 16, a capsular ligament 20, FIG. 3, the glenoid labrum 22, the articular cartilage of the acetabulum 24 and the joint space is indicated at 26.

The hip bone or femur 28, at its upper end, includes the trochanter major 30 to which the spherical-type femoral head 32 is attached. The femoral head is received within the acetabulum 14 engaging the cartilage the femoral head convex surface and the acetabular concave socket surface 16.

As shown in FIGS. 1-3, the prosthesis 24 of the invention comprises a body formed of a synthetic material such as a high density polyethylene. The prosthesis includes a gase 36 from which extends the flange 38 which overlaps the ilium adjacent to the acetabular rim 18. At the other edge of the prosthesis a lip 40 is defined which extends beyond the acetabular rim 18, and the lip 40 and base 36 are formed with a concave inner surface 42 which is complementary to the configuration of the acetabular socket surface 16 as to define an extension thereof and form a shelf.

The prosthesis is affixed to the ilium by multiple fasteners 44 extending through the flange 38 into the bone of the ilium. It will be appreciated that the fasteners 44 may be in the form of screws, staples or other fastening means commonly employed to surgically attach components to bone.

As the prosthesis lip 40 extends beyond the acetabular rim 18 as significant distance, and extends beyond the acetabular rim primarily posteriorly and superiorly the prosthesis inner surface 42 provides an effective surface for engaging with the femoral head 32 to retain the femoral head within the acetabulum regardless of the angular position of the femur 28 to the ilium 12. Thus, the prosthesis renders a previously unstable hip joint stable.

By enclosing the femoral head in a manner very similar to a normal acetabulum the prosthesis destributes the forces acting on a deficient acetabulum in such a manner as to promote a more normal molding of the acetabular roof surface with growth as is particularly desirable with a growing child. The use of the prosthesis also encourages the normal shaping of the femoral head as is highly desirable with a growing child.

The extracapsular configuration of the prosthesis eliminates the need for highly accurate geometrical fits between the femoral head and the ilium as are required in a total joint replacement, and the use of the described prosthesis provides an alternative to complex surgical procedures currently employed to correct many types of hip joint deficiencies.

It will be appreciated that various modifications to the inventive concepts will be apparent to those skilled in the art without departing from the spirit and scope thereof.

We claim:

1. An extracapsular prosthesis designed to serve as an adjunct to an existing natural socket comprising:
a curvilinear shell configured to extend laterally, posteriorly and superiorly beyond the acetabulum including an elongated base having a concave inner surface and an outer surface, a flange extending substantially along the outer surface and outwardly from said base to overlap the natural ilium, said flange adapted to receive means for attaching the shell to the ilium exterior adjacent to the natural socket, a lip extending from said base opposite said flange, said lip having an inner concave surface extending posteriorly and superiorly beyond the acetabular rim wherein the combination of said lip and said base form a substantially continuous concave inner surface which is complimentary to the surface configuration of the natural socket thereby defining an extracapsular extension to retain the femoral head within the natural socket.

2. In an extracapsular prosthesis as in claim 1, said body being formed of a synthetic plastic material.

3. In an extracapsular prosthesis as in claim 2, said synthetic material comprising high density polyethylene.

4. The method of enhancing the existing natural socket defined in the ilium for improving the retention of the femoral head by extending the socket configuration of the acetabulum comprising the step of attaching a prosthesis to the ilium at the rim of the acetabulum extending posteriorly and superiorly beyond the acetabular rim having a femoral head conforming and engaging surface constituting a continuation of the natural socket whereby the prosthesis defines an extracapsular extension of the acetabulum and aids the retention of the femoral head within the acetabulum.

5. The method of enhancing the acetabulum as in claim 4 wherein the attaching of the prosthesis to the ilium comprises the step of mechanically attaching the prosthesis to the ilium by fasteners.

* * * * *